United States Patent [19]

Ensign

[11] 4,453,552
[45] Jun. 12, 1984

[54] ELECTRONIC BODY TEMPERATURE INDICATOR

[76] Inventor: John D. Ensign, 750 S. Main St., Brigham City, Utah 84302

[21] Appl. No.: 276,049

[22] Filed: Jun. 22, 1981

[51] Int. Cl.³ .................... A61B 5/00; G01K 7/12; A61M 16/00
[52] U.S. Cl. .................... 128/736; 374/181; 128/207.14
[58] Field of Search .............. 128/718, 724, 725, 727, 128/736; 73/341, 343 B, 359, 361, 362.4; 136/211, 212, 222, 224, 227; 374/179, 181, 208–210

[56] References Cited

U.S. PATENT DOCUMENTS

| | | | |
|---|---|---|---|
| 3,232,288 | 2/1966 | Krobath | 128/724 |
| 3,596,518 | 8/1971 | Kirkpatrick | 73/341 |
| 3,735,752 | 5/1973 | Rodder | 128/724 |
| 3,880,591 | 4/1975 | Burroughs | 128/716 |
| 3,903,743 | 9/1975 | Noller | 73/361 |
| 4,138,360 | 7/1979 | Adams | 128/725 |
| 4,210,155 | 7/1980 | Grimes | 128/727 |
| 4,305,388 | 12/1981 | Brisson | 128/736 |

OTHER PUBLICATIONS

S. A. Safronnikov, *Thermocouple for Precision Measurements on Industrial Objects*, Feb. 1970, 239–242.

Primary Examiner—Henry J. Recla
Assistant Examiner—Karin M. Reichle
Attorney, Agent, or Firm—A. Ray Osburn

[57] ABSTRACT

An electronic human body temperture indicator comprising a thermocouple, the hot junction of which is housed within a tube through which the patient's breath is exhaled. The cold junction is positioned in contact with the ambient air, and an adjacent ambient temperature air sensor is provided. An appropriate electronic package processes thermocouple and air temperature sensor output to provide a display of the patient's peak breath temperature. A breath outlet check valve prevents cross contamination by blocking inhalation through the indicator. A disposable breath inlet tube makes sterilization unnecessary between uses from patient to patient. According to one aspect of the invention, the indicator may be adapted for anesthesiology use, the hot junction then being located in an elbow connecting the gas supply tube and the disposable treachea tube.

17 Claims, 5 Drawing Figures

ELECTRONIC BODY TEMPERATURE INDICATOR

BACKGROUND OF THE INVENTION

1. Field:

The field of the invention is electronic devices for indicating the temperature of the human body.

2. State of the Art:

The shortcomings of conventional expanding liquid medical thermometers include the excessive time (three to four minutes) required, questionable precision and accuracy of the temperature indication, and the necessity for sterilization after use. Busy medical personnel often do not allow sufficient time for these thermometers to reach complete equilibrium readings. Other variables producing inaccuracy include the selection of measurement location upon or within the patient's body, since local body temperatures vary significantly. Even within the mouth, under the tongue, the temperature may vary as much as 1.5° F. from front to rear. Temperatures within the mouth also vary rapidly and significantly from evaporation of mouth fluids, if any air enters from the lips or the throat. Electronic temperature indicator probes have been developed for use within the body, utilizing thermocouples or thermistors as the basic temperature sensing elements. Such probes provide greatly improved (reduced) measuring periods, because of the very low mass of the thermocouple junctions or thermistor elements. Potentially, these junctions reach equilibrium generated electromotive force within small fractions of a second. Unfortunately, the junctions must be protectively housed, adding mass, slowing the measurement to about 1.5 to 2.5 minutes to complete equilibrium. In practice, these probes are generally allowed to remain in temperature sensing position for slightly less than one minute, the true temperature then being predicted from the reading using curves or other correction procedures based on questionable assumptions, often not accounting for the actual temperature measuring conditions. To shorten the temperature measuring time, the housings are of small diameter and elongate, being finely drawn and sharp, unpleasant and even dangerous in use. Sterilization is necessary between uses and the aforesaid variations with temperature sensing location are present.

BRIEF SUMMARY OF THE INVENTION

With the foregoing in mind, the disadvantages of prior art devices for indicating body temperature are eliminated or substantially alleviated by providing such a device comprising a thermocouple with a hot junction directly bathed by the patient's expelled breath, reaching full breath temperature in a small fraction of a second. The output electromotive force of the thermocouple may then be converted through conventional electronic means into a readout display of the peak temperature of the exhaled breath, which is well established to be predictably related to the core temperature of the body. Breath tube means is provided to direct a flow of exhaled breath from the patient's mouth to immerse the junction undiluted by any mixing ambient air. Check valve means is provided to prevent any contamination of the patient from inhaling through the device. The breath tube is detachable and disposable so that no sterilization is required. For general medical use, it is convenient that the device be capable of use in locations of varying ambient air temperature, without an ice bath or other constant temperature reference. Therefore, it is preferable that the cold junction be positioned to sense ambient air temperature, and that an adjacent air temperature sensor be provided, also adapted to communicate with the electronics. According to another aspect of the invention, the breath sensing thermocouple junction may be disposed within, for instance, an elbow providing connecting passage means between the disposable trachea tube and the gas supply hose used in gas anesthesiology. Means may also be provided to sense and compensate for patient breathing rate, when extremely accurate temperature indications are required.

It is therefore a principal object of the invention to provide an economical body temperature indicator with insignificant delay time, which automatically compensates for ambient air temperature, indicates body temperature extremely consistently and accurately, and does not require sterilization between uses from one patient to another.

BRIEF DESCRIPTION OF THE DRAWINGS

In the drawings, which represent the best mode presently contemplated for carrying out the invention.

DETAILED DESCRIPTION OF ILLUSTRATED EMBODIMENTS

Figure 1:
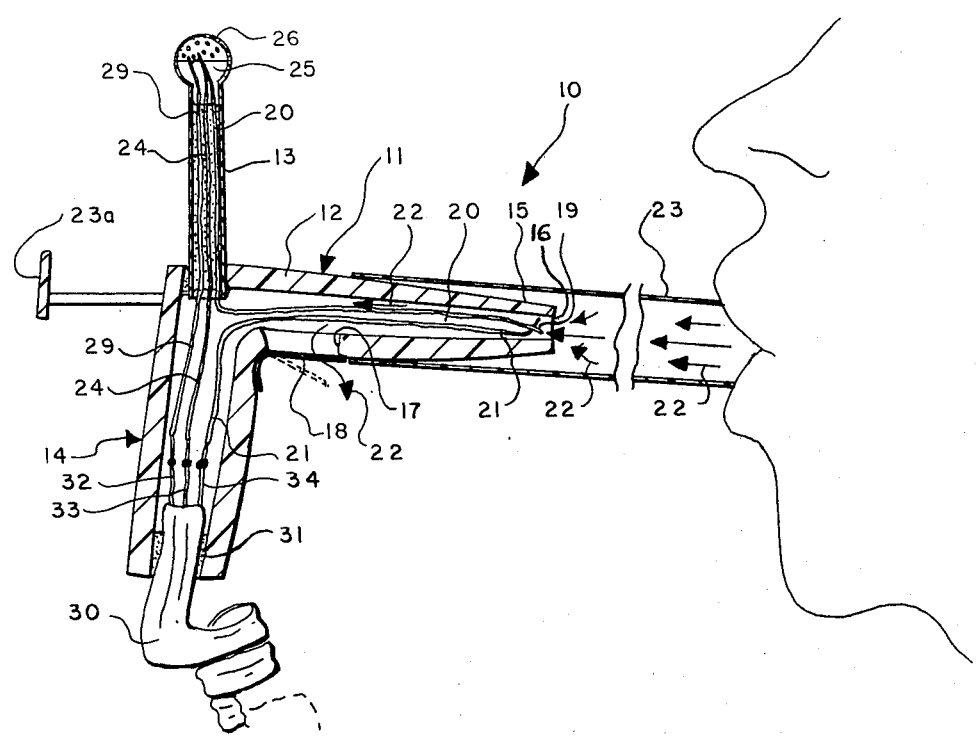
FIG. 1 is a cross sectional view of an electronic breath temperature indicator in accordance with the invention, drawn to approximately full scale, FIG. 2 an enlarged sectional view of a fragment of the indicator of FIG. 1, drawn to a larger scale, showing the cold junction of the thermocouple and the adjacent ambient air temperature sensor, FIG. 3 a schematic representation of the electronic temperature indicator adapted for use in gas anesthesiology, FIG. 4 an enlarged sectional view of the hot junction containing elbow of the embodiment of FIG. 3, and FIG. 5 a schematic block diagram of the electronic package adapted for use in conjunction with the electronic body temperature indicator of the invention.
Figure 5:
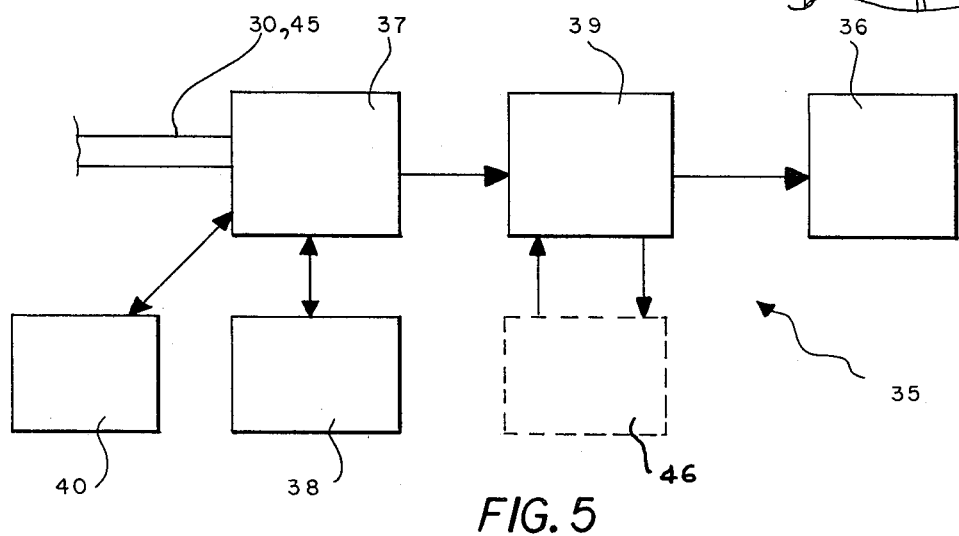

The illustrative embodiment of the body temperature indicator 10 shown in FIG. 1 comprises a tubular housing 11, elbow shaped for handling convenience, having a breath receiving branch tube 12, an elongate tubular stack 13 and an electrical cord branch 14. End 15 of breath branch 12 has a breath entrance 16. At the opposite end of branch 12, a breath outlet orifice 17 is provided, closed by a reed check valve 18. A bi-metallic thermocouple hot juction 19 (of thermocouple wire 20 and hot junction lead wire 21) is disposed within the end 15 of branch 12 near breath entrance 16 so as to be within a stream of exhaled breath (arrows 22) of the patient. A removable and disposable mouth tube 23 frictionally engages breath branch 12 sealably. Sliding thumb plunger 23a may be provided for sanitary removal of tube 23 after use. Thermocouple wire 20 is joined to cold junction lead wire 24 to form cold junction 25 exposed to the ambient air at the outer end of stack 13, inside perforated protective cover 26. Cold junction 25 is shielded by epoxy 27 in stack 13 from any heat tending to be conducted from breath branch 12. A thermistor 28, illustratively of the bead type, is connected between a thermistor lead wire 29 and a cold junction lead wire 24 at the outstanding end of the stack 13. A three wire electrical cord 30, advantageously of the coil type, is secured as by adhesive 31 within cord branch 14, having wires 32, 33 and 34 respectively connected to thermistor lead 29, cold junction lead 24 and hot junction lead 21. Wires 32, 33 and 34 of cord 30 are electrically connected at their remote ends to an electronic package 35, shown in FIG. 1 and indicated schematically in block diagram FIG. 5. Elecronic package 35 includes a visual display 36 to indicate body temperature of the patient. Completely exposed hot junction 19 reaches breath temperature in a small fraction of a second. Cold junction 25 responds equally rapidly to local ambient air temperature. The electromotive force (e.m.f.) generated by the cold and the hot junction is sensed by the electronic package 35 through conductor leads 33 and 34, and increased in magnitude by voltage amplifier 37. (FIG. 5) Air temperature compensating electronics 38 are provided to correct for the effects of level of temperature (ambient) of cold junction 25 upon the e.m.f. felt by amplifier 37. The compensating electronics 38 may utilize temperature sensing diodes, thermisters of thermocouple type sensors, arranged to correctively offset the breath temperature readout. The air temperature information (cold junction temperature) is provided by the thermistor 28. An e.m.f. peak detector 39 is provided, triggering the digital display 36 of the temperature of the patient's exhaled breath. Peak temperature display 36 is maintained for the convenience of medical personnel. Since air leaving the lungs has been proven to accurately correspond to body core temperature, and the peak temperature of exhaled air at the mouth is predictably offset therefrom, an accurate readout display 36 is produced. The variations in indicated body temperature common to other body temperature sensing devices, such as location in the body and evaporative cooling within the mouth, are thus eliminated by the use of temperature indicator 10. In applications of indicator 10 requiring extremely precise body temperature measurements, the very small breath temperature variations attributable to breathing rate (breath flow rate) may be compensated for by appropriate circuitry 40. (FIG. 5) Data establishing these variations have been empirically derived. Such circuitry 40 may include breath frequency sensing (inhalations per minute, e.g.) components and be adapted to provide appropriate corrective offset to the breath temperature readout. Alternately, breath flow rate may be sensed, upon which to base the corrective offset.

The cold junction 25 need not be located as in stack 13 of FIG. 1, but could, in other embodiments of indicator 10, be located elsewhere for the convenience of the designer and user. The cold junction 25 and the thermistor 28 (or other room air temperature sensing means) could, for example, be within the electronic package 35, suitably ventilated. The conventional electric cord 30 with conventional copper wires would then be replaced with a coil cord having wires of themocouple material. The embodiment shown in FIG. 1 permits the convenient and economical use of the conventional copper wire coil cord 30, however.

In the embodiment of temperature indicator 10 illustrated in FIG. 1, it is convenient and advantageous to employ a copper-constantan thermocouple, since cold junction lead 24 and hot junction lead 21 are of copper, compatible with the copper wires 32, 33 and 34 of conventional cord 30. However, by the application of well known thermocouple design principles, other types of bi-metallic thermocouples may be employed equally effectively, as for example, the chromel-constantan type.

Figure 3:
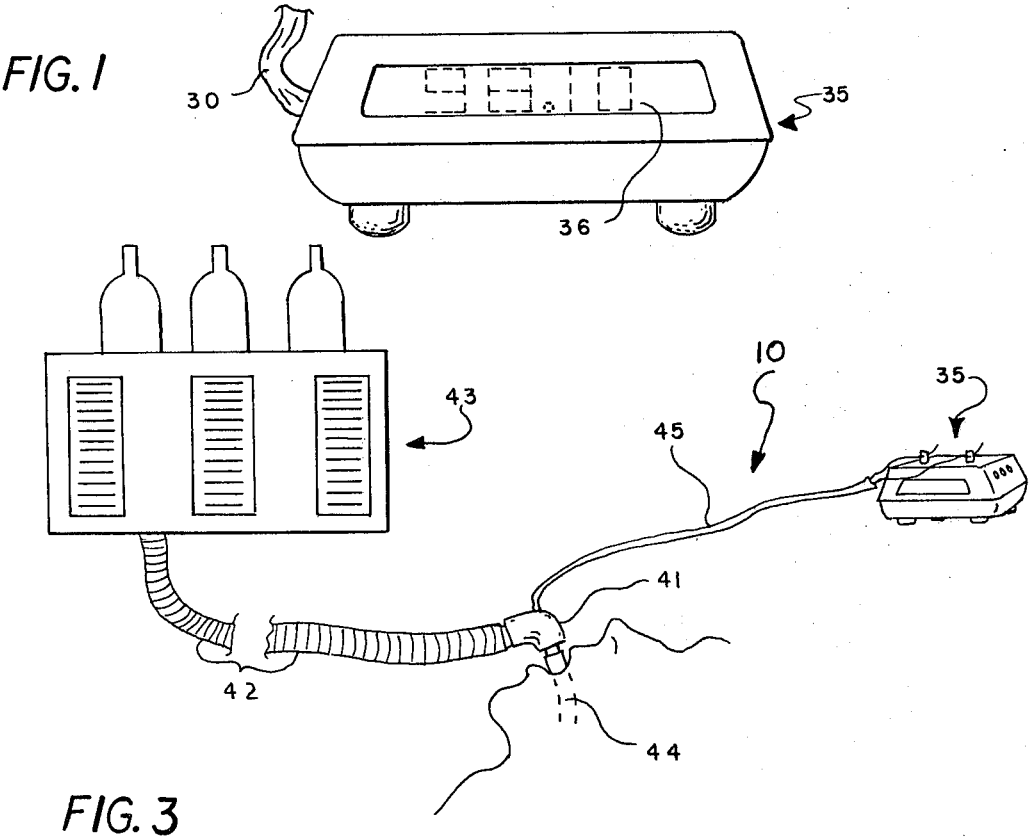
Figure 4:
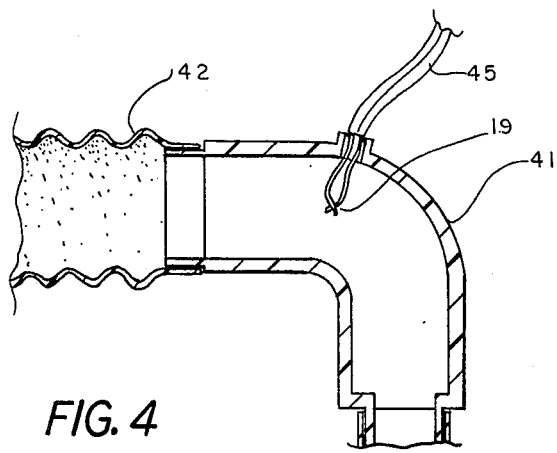
Figure 2:
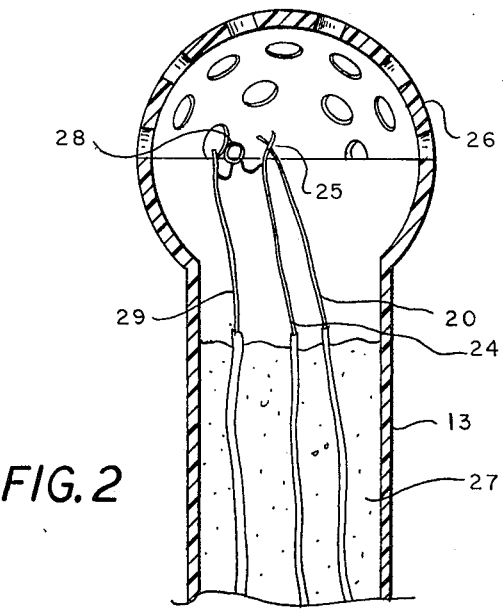

An embodiment of temperature indicator 10 adapted for use in gas anesthesiology is illustrated in FIGS. 3 and 4. Hot junction 19 is placed in a tubular member 41 adapted to connect the anesthetic gas supply tube 42 from gas control unit 43 to the disposable trachea tube 44. The ambient air sensing and compensation features are located in box 38. Therefore, it is especially convenient and advantageous to utilize readily available thermocouple lead cord having, for example, insulated copper and constantan wires, the cold junction 25 being contained in the electronic package 35. It is desirable in this application to provide display reset capability 46.

The invention may be embodied in other specific forms without departing from the spirit or essential characteristics thereof. The present embodiment is therefore to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed and desired to be secured by United States Letters Patent is:

1. A body temperature indicator, comprising:
    thermocouple means having a hot junction and a cold junction;
    means for positioning the hot junction so that the exhaled breath of a patient flows thereover in direct contact therewith, said means comprising tubular means having a central passage therethrough, the hot junction positioned within said central passage, said tubular means having an open end for the patient to expel breath into the passage, and breath outlet orifice means, so that the breath flows through the passage about the hot junction in direct contact therewith; and air flow check valve means at the outlet orifice means, for preventing the patient from inhaling through the passage of the tubular means;
    means for positioning the cold junction in direct contact with the ambient air remotely from the breath of the patient;
    ambient air temperature sensing means adjacent the cold junction; and
    means for indicating the temperature utilizing electrical input from said thermocouple means and said ambient air temperature sensing means.

2. The indicator of claim 1, wherein:
    said tubular means comprises a junction containing portion, and mouth contacting portion adapted for removable securement sealably to the junction containing portion, said mouth contacting portion being disposable.

3. The indicator of claim 2 wherein:
    the means positioning the cold junction and the ambient air temperature sensing means comprises tubular stack means outwardly projecting from the junction containing portion of the tubular means.

4. The indicator of claim 2, wherein:
    said temperature indicating means comprises electronic means for processing the electromotive force from the thermocouple together with ambient air temperature information provided by the ambient air temperature sensing means, so as to compensate said electromotive force for the effect of ambient air temperature and to provide a readout of the body temperature of the patient.

5. The indicator of claim 4, wherein:

the electronic means comprises portable packaging means therefor; and the cold junction and the ambient air temperature sensing means are incorporated into the packaging means.

6. The indicator of claim 5, wherein:

the wires of the hot junction extend from the tubular means to said portable packaging means.

7. The indicator of claim 4, wherein:

the dissimilar metals of the thermocouple are copper and constantan.

8. The indicator of claim 4, wherein:

said electronic means comprises portable packaging means, therefor; the cold junction and the ambient air temperature sensing means are incorporated into the packaging means; and the wires of the hot junction extend from the tubular means to said portable packaging means.

9. The indicator of claim 1, wherein:

the means positioning the cold junction and the ambient air temperature sensing means comprises tubular stack means outwardly projecting from the tubular means.

10. The indicator of claim 9, wherein:

said temperature indicating means comprises electronic means for processing the electromotive force from the thermocouple together with ambient air temperature information provided by the ambient air temperature sensing means, so as to compensate said electromotive force for the effect of ambient air temperature and to provide a readout of the body temperature of the patient.

11. The indicator of claim 10, wherein:

the eletronic means comprises portable packaging means therefor.

12. The indicator of claim 10, wherein:

the dissimilar metals of the thermocouple are copper and constantan.

13. The indicator of claim 1, wherein:

said temperature indicating means comprises electronic means for processing the electromotive force from the thermocouple together with ambient air temperature information provided by the ambient air temperature sensing means, so as to compensate said electromotive force for the effect of ambient air temperature and to provide a readout of the body temperature of the patient; and wherein said electronic means comprises portable packaging means, therefor;

the cold junction and the ambient air temperature sensing means are incorporated into the packaging means; and the wires of the hot junction extend from the tubular means to said portable packaging means.

14. The indicator of claim 2, wherein:

said temperature indicating means comprises electronic means for processing the electromotive force from the thermocouple together with ambient air temperature information provided by the ambient air temperature sensing means, so as to compensate said electromotive force for the effect of ambient air temperature and to provide a readout of the body temperature of the patient; and wherein said electronic means comprises portable packaging means, therefor; the cold junction and the ambient air temperature sensing means are incorporated into the packaging means; and the wires of the hot junction extend from the tubular means to said portable packaging means.

15. A body temperature indicator, comprising:

thermocouple means having a hot junction and a cold junction;

means for positioning the hot junction so that the exhaled breath of a patient flows thereover in direct contact therewith, said means comprising tubular means having a central passage therethrough, the hot junction positioned within said central passage, said tubular means having a first open end for the patient to expel breath into the passage, a second open end, so that the breath flows through the passage about the hot junction in direct contact therewith; said first and second open ends adapted to be connected to the passages of a disposable trachea tube and an anesthetic gas supply hose, respectively;

means for positioning the cold junction in direct contact with the ambient air remotely from the breath of the patient;

ambient air temperature sensing means adjacent the cold junction; and means for indicating the temperature utilizing electrical input from said thermocouple means and said ambient air temperature sensing means.

16. The indicator of claim 15, wherein:

said temperature indicating means comprises electronic means for processing the e.m.f. from the thermocouple together with ambient air temperature information provided by the ambient air temperature sensing means, so as to compensate said e.m.f. for the effect of ambient air temperature and to provide a readout of the body temperature of the patient, said electronic means comprising means compensating the e.m.f. for the breath flow rate of the patient.

17. The indicator of claim 1, wherein:

the electronic means comprises portable packaging means therefor;

the cold junction and the ambient air temperature sensing means are incorporated into the packaging means; and the wires of the hot junction extend from the tubular means to said portable packaging means.

* * * * *